United States Patent
Dolloff et al.

(10) Patent No.: US 10,329,269 B2
(45) Date of Patent: Jun. 25, 2019

(54) INDENE DERIVATIVES AND USES THEREOF

(71) Applicant: MUSC FOUNDATION FOR RESEARCH DEVELOPMENT, Charleston, SC (US)

(72) Inventors: Nathan G. Dolloff, Mt. Pleasant, SC (US); Reeder M. Robinson, Charleston, SC (US); Allen B. Reitz, Lansdale, PA (US); Haiyan Bian, Princeton, NJ (US)

(73) Assignees: Leukogene Therapeutics Incorporated, Mt. Pleasant, SC (US); MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 16/115,780

(22) Filed: Aug. 29, 2018

(65) Prior Publication Data
US 2019/0062298 A1    Feb. 28, 2019

Related U.S. Application Data

(60) Provisional application No. 62/552,449, filed on Aug. 31, 2017.

(51) Int. Cl.
| | | |
|---|---|---|
| *C07D 317/70* | (2006.01) | |
| *C07C 39/38* | (2006.01) | |
| *C07D 319/14* | (2006.01) | |
| *C07D 263/52* | (2006.01) | |
| *C07C 69/712* | (2006.01) | |
| *A61P 35/00* | (2006.01) | |
| *C07C 62/32* | (2006.01) | |
| *C07C 69/757* | (2006.01) | |
| *C07C 235/40* | (2006.01) | |
| *C07C 235/34* | (2006.01) | |
| *C07C 49/255* | (2006.01) | |
| *C07C 59/72* | (2006.01) | |

(52) U.S. Cl.
CPC .......... *C07D 317/70* (2013.01); *A61P 35/00* (2018.01); *C07C 39/38* (2013.01); *C07C 49/255* (2013.01); *C07C 59/72* (2013.01); *C07C 62/32* (2013.01); *C07C 69/712* (2013.01); *C07C 69/757* (2013.01); *C07C 235/34* (2013.01); *C07C 235/40* (2013.01); *C07D 263/52* (2013.01); *C07D 319/14* (2013.01)

(58) Field of Classification Search
CPC ..................................................... C07D 317/70
USPC ........................................................ 549/200
See application file for complete search history.

(56) References Cited

U.S. PATENT DOCUMENTS

| | | |
|---|---|---|
| 4,568,782 A | 2/1986 | Pagnotta et al. |
| 6,197,990 B1 | 3/2001 | Oda et al. |
| 7,595,362 B2 | 9/2009 | Kawabe et al. |

OTHER PUBLICATIONS

The International Search Report and Written Opinion, dated Dec. 18, 2018, in the corresponding PCT Appl. No. PCT/US18/48449.

*Primary Examiner* — Nizal S Chandrakumar

(57) ABSTRACT

The present invention relates to compounds of formula (I):

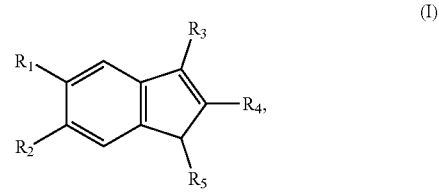

including any stereochemically isomeric form thereof, or pharmaceutically acceptable salts thereof, for the treatment of, for example, cancer.

2 Claims, 5 Drawing Sheets

| MM.1S BzR | (−) Btz | (+) 20 nM Btz | |
|---|---|---|---|
| | EC$_{50}$ μM | EC$_{50}$ μM | PDI IC$_{50}$ μM |
| E64FC26 | 1.9 ± 0.2 | 0.68 ± 0.06 | 0.60 ± 0.04 |
| E64FC40 | 1.6 ± 0.1 | 0.46 ± 0.02 | |
| E64FC41 | 2.03 ± 0.06 | 0.58 ± 0.02 | |
| E64FC42 | 3.08 ± 0.09 | 0.89 ± 0.05 | 1.04 ± 0.06 |
| E64FC43 | 1.8 ± 0.4 | 0.60 ± 0.06 | |
| E64FC44 | 1.8 ± 0.3 | 0.50 ± 0.02 | |
| E64FC45 | 6.9 ± 0.8 | 3.5 ± 0.1 | 1.5 ± 0.1 |
| E64FC46 | 7.9 ± 0.5 | 3.2 ± 0.4 | |
| E64FC47 | 1.6 ± 0.2 | 0.50 ± 0.02 | |
| E64FC49 | 0.85 ± 0.07 | 0.142 ± 0.004 | 1.12 ± 0.05 |
| E64FC50 | 1.3 ± 0.1 | 0.199 ± 0.006 | 1.4 ± 0.1 |
| E64FC51 | 3.0 ± 0.2 | 0.41 ± 0.02 | |
| E64FC52 | >5 | 2.4 ± 0.4 | |
| E64FC53 | >5 | 2.1 ± 0.4 | |
| E64FC54 | >5 | 4.1 ± 0.5 | |
| E64FC58 | 0.721 ± 0.008 | 0.192 ± 0.006 | 0.66 ± 0.01 |
| E64FC59 | 3.4 ± 0.2 | 0.65 ± 0.05 | 1.91 ± 0.05 |
| E64FC60 | 3.0 ± 0.2 | 1.6 ± 0.1 | |
| E64FC61 | 3.1 ± 0.3 | 1.02 ± 0.07 | |
| E64FC62 | >5 | >5 | |
| E64FC63 | >5 | >5 | |
| E64FC64 | 1.50 ± 0.05 | 0.47 ± 0.02 | |
| E64FC65 | 1.11 ± 0.03 | 0.23 ± 0.01 | 0.79 ± 0.06 |
| E64FC66 | 3.4 ± 0.4 | 1.04 ± 0.07 | |
| E64FC67 | 5.8 ± 0.3 | 1.04 ± 0.06 | 20.4 ± 3.1 |
| E64FC68 | 2.1 ± 0.2 | 0.54 ± 0.03 | |
| E64FC69 | 2.6 ± 0.2 | 1.8 ± 0.2 | |
| E64FC70 | >5 | >5 | |
| E64FC72 | ~3.2 | ~2.5 | |
| E64FC73 | 3.0 ± 0.4 | 1.12 ± 0.09 | 1.00 ± 0.05 |
| E64FC74 | 0.84 ± 0.03 | 0.201 ± 0.008 | |
| E64FC75 | 0.79 ± 0.01 | 0.144 ± 0.004 | |
| E64FC76 | 1.88 ± 0.09 | 0.66 ± 0.06 | |
| E64FC77 | 1.70 ± 0.08 | 0.68 ± 0.05 | |
| E64FC78 | 1.44 ± 0.06 | 0.42 ± 0.05 | |
| E64FC79 | ~1.2 | 0.214 ± 0.006 | |
| E64FC80 | ~1.16 | 0.25 ± 0.01 | |
| E64FC81 | 0.83 ± 0.03 | 0.132 ± 0.006 | 0.68 ± 0.02 |
| E64FC82 | 10.8 ± 1.9 | 1.5 ± 0.1 | 11.5 ± 2.1 |
| E64FC83 | 3.2 ± 0.2 | 0.89 ± 0.04 | |
| E64FC84 | >5 | 1.7 ± 0.2 | 17.6 ± 2.5 |
| E64FC85 | 1.5 ± 0.1 | 0.29 ± 0.01 | |
| E64FC86 | 1.4 ± 0.1 | 0.52 ± 0.05 | |
| E64FC87 | 1.45 ± 0.07 | 0.23 ± 0.02 | |
| E64FC88 | 1.0 ± 0.1 | 0.17 ± 0.01 | |
| E64FC89 | 1.7 ± 0.2 | 0.21 ± 0.01 | |
| E64FC90 | 1.5 ± 0.3 | 0.28 ± 0.02 | |
| E64FC91 | 2.1 ± 0.2 | 0.289 ± 0.007 | |
| E64FC93 | 1.1 ± 0.1 | 0.16 ± 0.01 | |
| E64FC94 | 1.3 ± 0.1 | 0.275 ± 0.008 | |
| E64FC95 | 1.4 ± 0.1 | 0.29 ± 0.02 | |

FIG. 5

INDENE DERIVATIVES AND USES THEREOF

STATEMENT REGARDING FEDERALLY SPONSORED RESEARCH OR DEVELOPMENT

This invention was made with Government support under P20GM103542, UL1TR001450, and R41CA213488. The Government has certain rights in the invention.

FIELD OF THE INVENTION

The invention relates generally to indene derivatives useful for the treatment of cancers and for reducing resistance to standard of care cancer therapy. All documents cited to or relied upon below are expressly incorporated herein by reference.

BACKGROUND OF THE INVENTION

Proteasome inhibitors (PIs) such as, for example, bortezomib, and histone deacetylase (HDAC) inhibitors such as, for example, panobinostat, are cornerstone agents in the treatment of multiple myeloma (MM). Acquired or inherent resistance to these agents represents a significant obstacle to sustained and durable responses in patients. A need exists in the art for new, targeted strategies that target and kill MM and other cancer cell types, as well as enhance the activity of other therapies in resistant cancer cells.

SUMMARY OF THE INVENTION

The present invention is directed to a compound of formula (I):

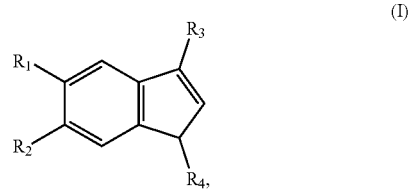

wherein:
$R_1$ and $R_2$, independently of each other, are hydrogen, hydroxyl, alkyl, alkoxy, methoxy-acetate, phosphate, valine, Gly-Ser, —OC(O)CH$_2$OC(O)CH$_3$, —OC(O)CH$_2$OCH$_3$, —OCH$_2$C(O)C(CH$_3$)$_3$, —OCH$_2$C(O)NH$_2$ or —OCH$_2$C(O)OH; or $R_1$ and $R_2$, together with the carbon atoms to which they are attached, form a 5 to 6-membered ring with one or two ring carbons replaced independently by oxygen or nitrogen;
$R_3$ is hydrogen, hydroxyl, halogen, cyano, —COOH, —C(O)NH$_2$, —C(O)CH$_2$CH$_3$, —C(O)-alkoxy, alkyl, alkoxy, halo-lower alkyl, carboxyl, amide, ester or nitrile; and
$R_4$ is alkyl or alkenyl, said alkyl or alkenyl optionally mono or bi-substituted independently with hydrogen, halogen, hydroxyl, —OCH$_2$-phenyl, cycloalkyl, —OCH$_2$-halophenyl or —OCH$_2$-phenylhaloalkyl,
or a pharmaceutically acceptable salt thereof.

The present invention is also directed to a pharmaceutical composition, comprising a therapeutically effective amount of a compound according to formula (I), or a pharmaceutically acceptable salt thereof, and a pharmaceutically acceptable carrier.

The present invention is further directed to a method for the treatment of cancer and enhancing the activity of standard of care cancer agents, exemplified here for therapy of multiple myeloma, and for reducing resistance to PIs, comprising the step of administering to a patient in need thereof a therapeutically effective amount of a compound according to formula (I), or a pharmaceutically acceptable salt thereof, and a pharmaceutically acceptable carrier.

BRIEF DESCRIPTION OF THE DRAWINGS

FIG. 5 shows activity data of representative compounds of the invention.

DETAILED DESCRIPTION OF THE INVENTION

Figure 1:
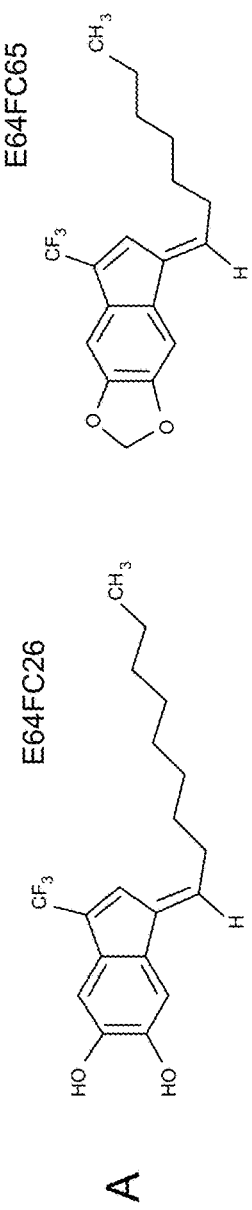
FIG. 1 provides data showing Proteasome Inhibitor re-sensitizing characteristics of compounds of the invention in resistant MM cells and various other cancer cell types.
Figure 1:
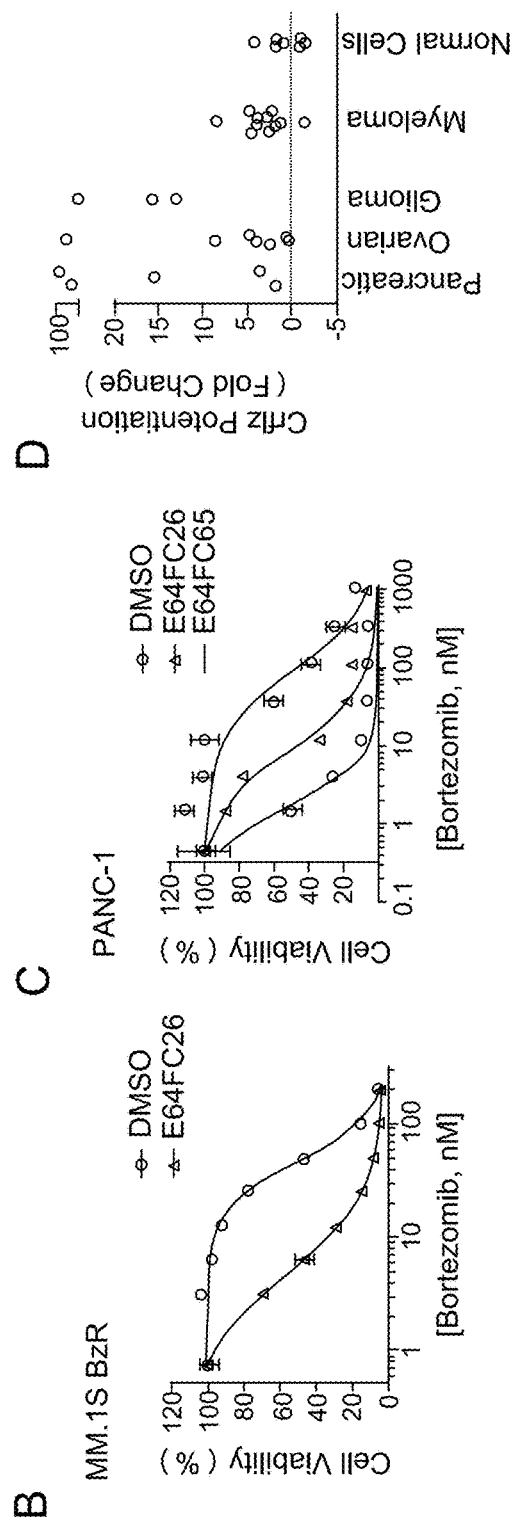

It is to be understood that the descriptions of the present invention have been simplified to illustrate elements that are relevant for a clear understanding of the present invention, while eliminating, for the purpose of clarity, many other elements found in typical pharmaceutical compositions. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The invention is directed to, for example, compounds that inhibit protein disulfide isomerase (PDI). The compounds of the invention demonstrate anti-tumor efficacy as single agents and enhance the activity of other targeted cancer therapeutics, including proteasome and HDAC inhibitors.

The inventors identified PDI as a promising target in cancer, including treatment resistant cancer. For example, the inventors identified compounds E64FC26:

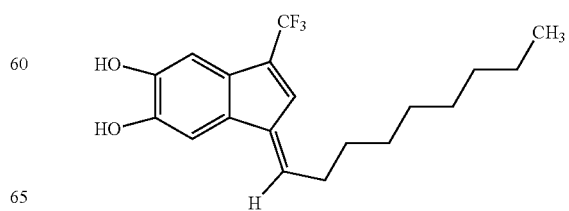

and E64FC65:

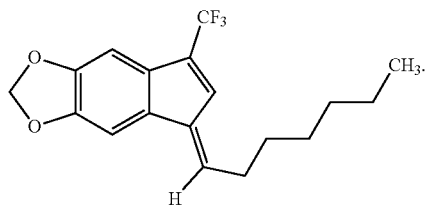 [SMILES: CCCCCC/C=C1\C=C(C(F)(F)F)c2cc3c(cc21)OCO3]

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

A compound according to the invention is inherently intended to comprise all stereochemically isomeric forms thereof. The term "stereochemically isomeric forms" as used hereinbefore or hereinafter defines all the possible stereoisomeric forms which the compounds of formula (I) and their N-oxides, pharmaceutically acceptable salts or physiologically functional derivatives may possess. Unless otherwise mentioned or indicated, the chemical designation of compounds denotes the mixture of all possible stereochemically isomeric forms. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention. Of special interest are those compounds of formula (I) which are stereochemically pure.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (I) is for instance specified as (R,S), this means that the compound is substantially free of the (S,R) isomer.

The compounds of formula (I) may be synthesized in the form of mixtures, in particular racemic mixtures, of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of formula (I) are meant to comprise those compounds of formula (I) wherein e.g. an enol group is converted into a keto group (keto-enol tautomerism). Tautomeric forms of the compounds of formula (I) or of intermediates of the present invention are intended to be embraced by the ambit of this invention.

The term "alkyl" as used herein denotes an unbranched or branched chain, saturated, monovalent hydrocarbon residue containing 1 to 20 carbon atoms. In one embodiment, the number of carbon atoms in the alkyl chain can be 2, 3, 4, 5, 6, 7, 8, 9, 10, 11, 12, 13, 14, 15, 16, 17, 18, 19 or 20 carbon atoms. In another embodiment, the number of carbon atoms in the alkyl chain can be from 5 to 16 and referred to as "($C_5$-$C_{16}$)alkyl." The term "lower alkyl" denotes a straight or branched chain hydrocarbon residue containing 1 to 6 carbon atoms. "$C_{1-20}$ alkyl" as used herein refers to an alkyl composed of 1 to 20 carbons. Examples of alkyl groups include, but are not limited to, lower alkyl groups include methyl, ethyl, propyl, i-propyl, n-butyl, i-butyl, t-butyl, pentyl, isopentyl, neopentyl, hexyl, heptyl, octyl, nonyl, decyl, undecyl, dodecyl, tridecycl and hexadecyl.

The term "alkenyl" as used herein denotes an unbranched or branched chain, saturated, monovalent hydrocarbon residue of from 2 to 24 carbon atoms with a structural formula containing at least one carbon-carbon double bond. In one embodiment, the number of carbon atoms in the alkenyl chain can be 2, 3, 4, 5, 6, 7, 8, 9, 10, 11, 12, 13, 14, 15, 16, 17, 18, 19 or 20 carbon atoms. In another embodiment, the number of carbon atoms in the alkenyl chain can be from 5 to 16 and referred to as "($C_5$-$C_{16}$) alkenyl."

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "halogen" as used herein means fluorine, chlorine, bromine or iodine. In one embodiment, halogen may be fluorine or bromine.

A "patient" is a mammal, e.g., a human, mouse, rat, guinea pig, dog, cat, horse, cow, pig, or non-human primate, such as a monkey, chimpanzee, baboon or rhesus monkey, and the terms "patient" and "subject" are used interchangeably herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "optionally substituted," as used in this disclosure, means a suitable substituent can replace a hydrogen bound to a carbon, nitrogen, or oxygen. When a substituent is oxo (i.e., =O) then 2 hydrogens on the atom are replaced by a single O. In one embodiment, an alkyl or lower alkyl group can substituted with, for example, —N$_3$, —C≡CH, phenyl or OH. It will be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables within any of the Formulae represented herein are permissible only if such combinations result in stable compounds or useful synthetic intermediates wherein stable implies a reasonable pharmacologically relevant half-life at physiological conditions.

Dosage and Administration:

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-do-decylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight, and most preferred 1.0 and about 15 mg/kg body weight per day. Thus, for administration to a 70 kg person, the dosage range in one embodiment would be about 70 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Compounds of the present invention can be prepared beginning with commercially available starting materials and utilizing general synthetic techniques and procedures known to those skilled in the art. Chemicals may be purchased from companies such as for example SigmaAldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; and Waters Corporation, Milford, Mass. Biotage, ISCO and Analogix columns are pre-packed silica gel columns used in standard chromatography.

EXAMPLES

The following examples further describe and demonstrate particular embodiments within the scope of the present invention. Techniques and formulations generally are found in *Remington's Pharmaceutical Sciences* (Mack Publishing Co., Easton, Pa.). The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Synthesis Protocol of E64FC26

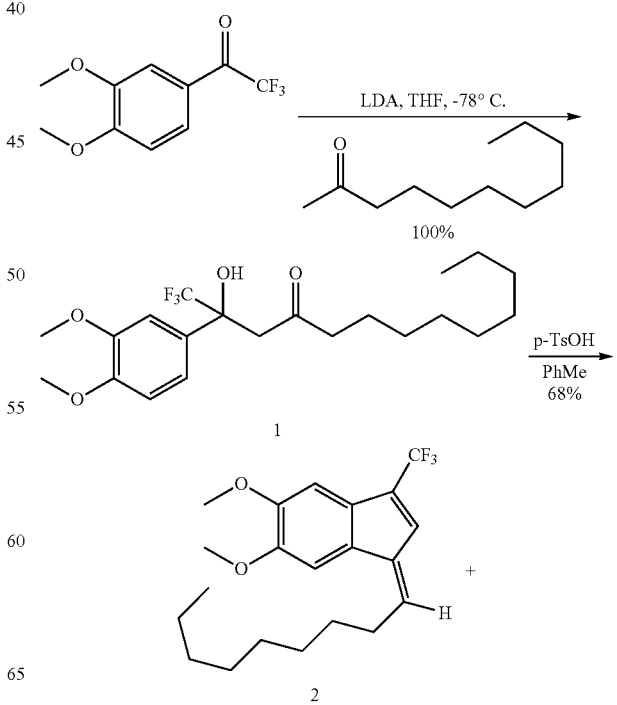

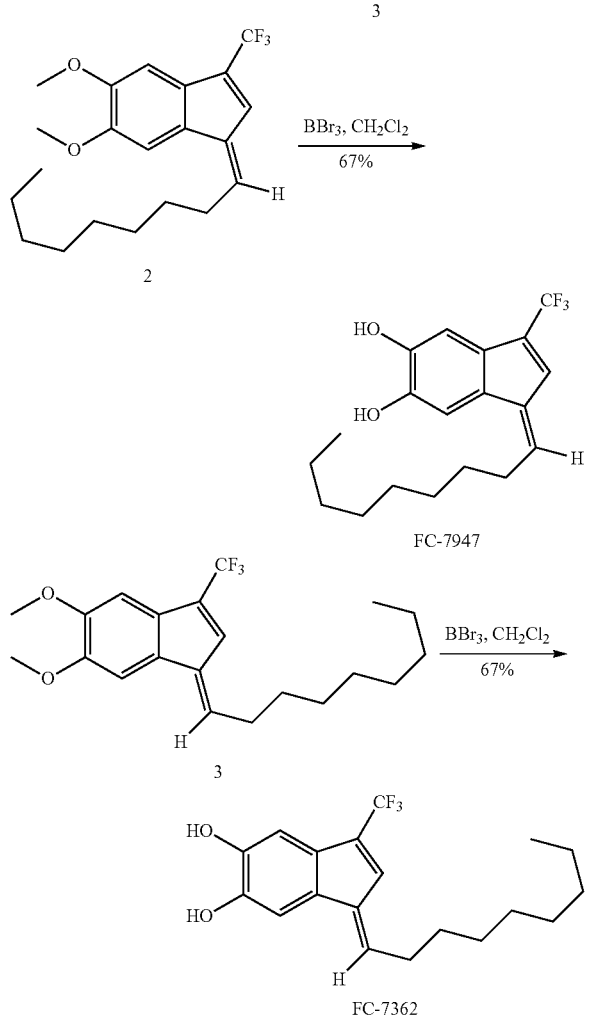

Step 1: 1,1,1-Trifluoro-2-hydroxy-2-(3,4-dimethoxyphenyl)tridecan-4-one (1)

A solution of undecan-2-one (306 mg, 1.8 mmol) in THF (8 mL) was cooled to −78° C., then LDA (2M solution in THF, 1.05 mL, 2.1 mmol) was added slowly. The mixture was stirred at −78° C. for 45 mins. A solution of 2,2,2-trifluoro-1-(3,4-dimethoxyphenyl)ethanone (234 mg, 1.0 mmol) in THF (2 mL) was added slowly. After stirred at −78° C. for 4 hrs, the mixture was warmed to RT for 30 mins. 20 mL of Sat'd aq. NH$_4$Cl was added. This mixture was extracted with diethyl ether (30 mL) twice. The combined ether layer was washed with brine (20 mL), dried over Na$_2$SO$_4$ and concentrated under vacuum. The residue was purified by ISCO flash column (0-10% ethyl acetate/hexanes to afford title compound 404 mg (100%/). LC/MS: R$_f$=6.88 min, purity >95%, (M+H)$^+$=404.68. $^1$H NMR (300 MHz, CDCl$_3$) δ 7.13-7.22 (m, 1H), 6.91-7.05 (m, 1H), 6.83 (d, J=8.50 Hz, 1H), 3.85 (s, 3H), 3.86 (s, 3H), 3.05-3.36 (m, 2H), 2.28-2.58 (m, 2H), 1.40-1.61 (m, 2H), 1.22 (br. s., 12H), 0.86 (t, J=6.45 Hz, 3H)

Step 2: (Z)-3-(Trifluoromethyl)-5,6-dimethoxy-1-nonylidene-1H-indene (2) and (E)-3-(trifluoromethyl)-5,6-dimethoxy-1-nonylidene-1H-indene (3)

The mixture of 1 (202 mg, 0.5 mmol), TsOH (48 mg, 0.25 mmol) in toluene (3 mL) was heated at 100° C. for 5 hrs. After reaction was done, the mixture was concentrated. The residue was purified by ISCO eluting with 0-10% ethyl acetate/hexanes to give the isomers (2: 34 mg; 3: 138 mg). LC/MS: R$_{f2}$=8.42 min, purity >95%, (M+H)$_2$$^+$=369.66. $^1$H NMR (300 MHz, CDCl$_3$) δ 7.29-7.40 (m, 1H), 6.96-7.04 (m, 1H), 6.72 (s, 1H), 6.41-6.60 (m, 1H), 3.92-4.03 (m, 6H), 2.73-2.92 (m, 2H), 1.58-1.81 (m, 2H), 1.24-1.56 (m, 10H), 0.77-1.02 (m, 3H); R$_{f3}$=8.27 min, purity >95%, (M+H)$^+$=369.66. $^1$H NMR (300 MHz, CDCl$_3$) δ 7.14-7.26 (m, 1H), 7.07 (br. s., 1H), 6.98 (s, 1H), 6.81 (t, J=7.91 Hz, 1H), 3.93-4.05 (m, 6H), 2.60 (q, J=7.42 Hz, 2H), 1.51-1.72 (m, 2H), 1.20-1.50 (m, 10H), 0.76-1.07 (m, 3H)

Step 3-1: (Z)-3-(Trifluoromethyl)-1-nonylidene-1H-indene-5,6-diol (FC-7947)

To a solution of in 2 (41 mg, 0.11 mmol) in CH$_2$Cl$_2$ (1 mL) was added 0.33 mL 1M BBr$_3$ solution in CH$_2$Cl$_2$ at −78° C. and stayed at −78° C. for 1 hr. The mixture was then warmed up to −20° C. for 1.5 hrs. TLC indicated the reaction was done. 4 mL NH4Cl and 5.0 mL ether were added. The organic layer was separated, dried, concentrated. The residue was purified to give FC-7947 (25 mg, 67% yield). LC/MS: R$_f$=6.93 min, purity >95%, (M+H)$^+$=341.64. $^1$H NMR (300 MHz, CDCl$_3$) δ 7.32-7.50 (m, 1H), 6.94-7.13 (m, 1H), 6.61-6.81 (m, 1H), 6.38-6.60 (m, 1H), 5.25-5.68 (m, 2H), 2.54-2.85 (m, 2H), 1.56-1.79 (m, 2H), 1.17-1.52 (m, 10H), 0.76-1.04 (m, 3H)

Step 3-2: (E)-3-(Trifluoromethyl)-1-nonylidene-H-indene-5,6-diol (FC-7362)

To a solution of 3 (158 mg, 0.43 mmol) in CH$_2$Cl$_2$ (5 mL) was added 1.3 mL 1M BBr$_3$ solution in CH$_2$Cl$_2$ at −78° C. and stirred at −78° C. for 1 hr. The mixture was then warmed up to −20° C. for 1.5 hrs. TLC indicated the reaction was done. 15 mL NH$_4$Cl and 30 mL ether were added. The organic layer was separated, dried, concentrated. The residue was purified by ISCO to give FC-7947 (96 mg, 65% yield). LC/MS: R$_f$=6.93 min, purity >95%, (M+H)$^+$=341.64. $^1$H NMR (300 MHz, CDCl$_3$) δ 7.10-7.23 (m, 1H), 7.00-7.09 (m, 1H), 6.98 (d, J=1.17 Hz, 1H), 6.62-6.77 (m, 1H), 2.46-2.65 (m, 2H), 1.46-1.68 (m, 2H), 1.20-1.45 (m, 10H), 0.79-1.02 (m, 3H).

Example 2

Synthesis Protocol of E64FC65

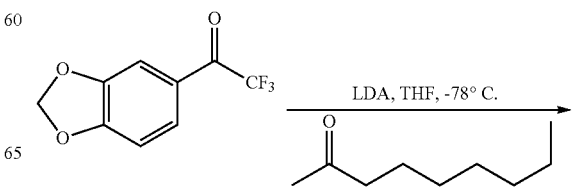

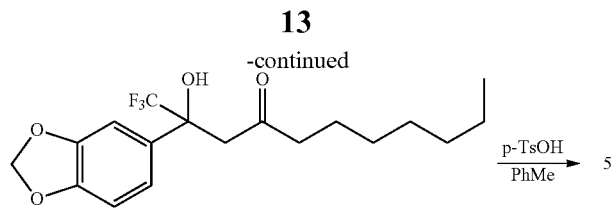

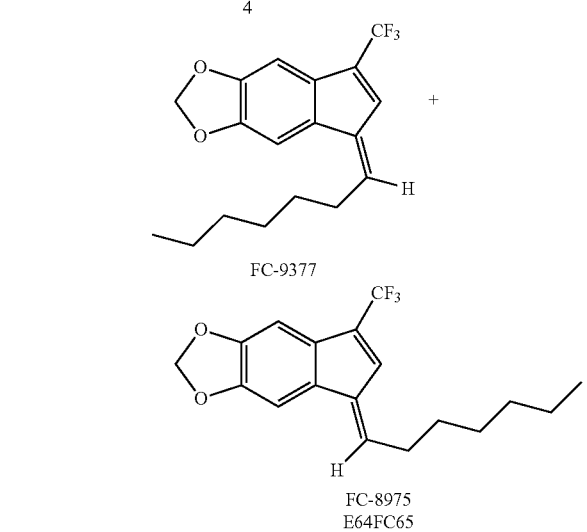

Step 1: 2-(benzo[d][1,3]dioxol-6-yl)-1,1,1-trifluoro-2-hydroxyundecan-4-one (4)

A solution of nonan-2-one (983 mg, 6.9 mmol) in THF (50 mL) was cooled to −78° C., and then LDA (2M solution in THF, 4.0 mL, 7.8 mmol) was added slowly. The mixture was stirred at −78° C. for 45 mins. A solution of 1-(benzo[d][1,3]dioxol-6-yl)-2,2,2-trifluoro ethanone (1.0 g, 4.6 mmol) in THF (5 mL) was added slowly. After stirred at −78° C. for 4 hrs, the mixture was warmed to RT for 30 mins. 100 mL of Sat'd aq. NH$_4$Cl was added. This mixture was extracted with diethyl ether (100 mL) twice. The combined ether layer was washed with brine (50 mL), dried over Na$_2$SO$_4$ and concentrated under vacuum. The residue was purified by ISCO flash column (0-10% ethyl acetate/hexanes to afford title compound 1.62 g (98%). LC/MS: R$_f$=6.70 min, purity >95%, (M)$^+$=360.61.

Step 2: (5Z)-7-(trifluoromethyl)-5-heptylidene-5H-indeno[5,6-d][1,3]dioxole (FC-9377) and (5E)-7-(trifluoromethyl)-5-heptylidene-5H-indeno[5,6-d][1,3]dioxole (FC-8975, E64FC65)

The mixture of 4 (1.62 g, 4.5 mmol), TsOH (387 mg, 2.25 mmol) in toluene (25 mL) was heated at 125° C. for 1.5 hrs. After reaction was done, the mixture was concentrated. The residue was purified by ISCO eluting with 0-10% ethyl acetate/hexanes to give the mixture (557 mg). This mixture was further purified by Gilson (75-100% MeCN/H$_2$O) to give the title compounds (FC-8975, 288 mg) and (FC-9377, 14 mg). LC/MS: R$_{f1}$=7.86 min, purity >95%, (M+H)$_1^+$=325.59. $^1$H NMR (300 MHz, CDCl$_3$) δ 7.04-7.14 (m, 2H), 7.01-7.07 (m, 1H), 6.86-6.99 (m, 1H), 6.65-6.82 (m, 1H), 5.99 (s, 2H), 2.46-2.68 (m, 2H), 1.47-1.70 (m, 2H), 1.17-1.46 (m, 7H), 0.79-0.99 (m, 3H)

R$_{f2}$=7.94 min, purity >95%, (M)$^+$=324.64. $^1$H NMR (300 MHz, CDCl$_3$) δ 7.09 (s, 1H), 6.94 (s, 1H), 6.68-6.69 (m, 1H), 6.49 (t, J=7.32 Hz, 1H), 6.00 (s, 2H), 2.70 (q, 2H), 1.59-1.66 (m, 2H), 1.30-1.35 (m, 6H), 0.87-0.92 (m, 3H)

Example 3

Synthesis Protocol of Additional Compounds of the Invention

Using the procedures in Examples 1 and 2 above, the following compounds were also be prepared:

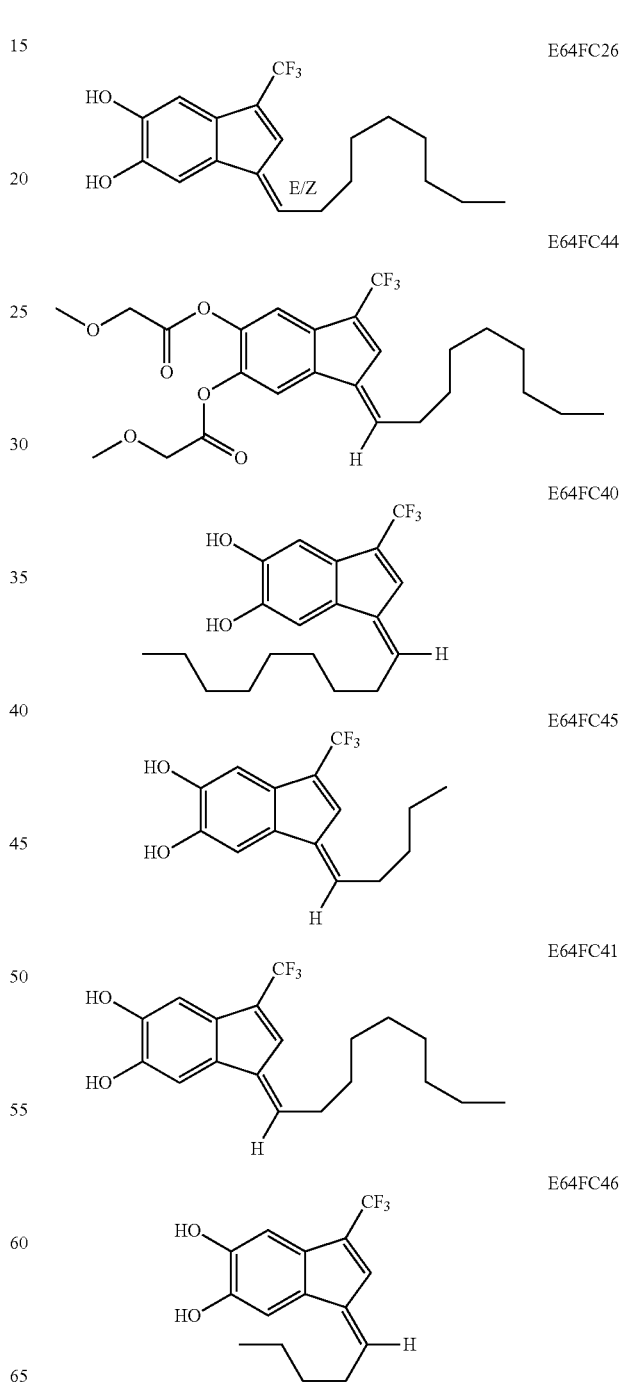

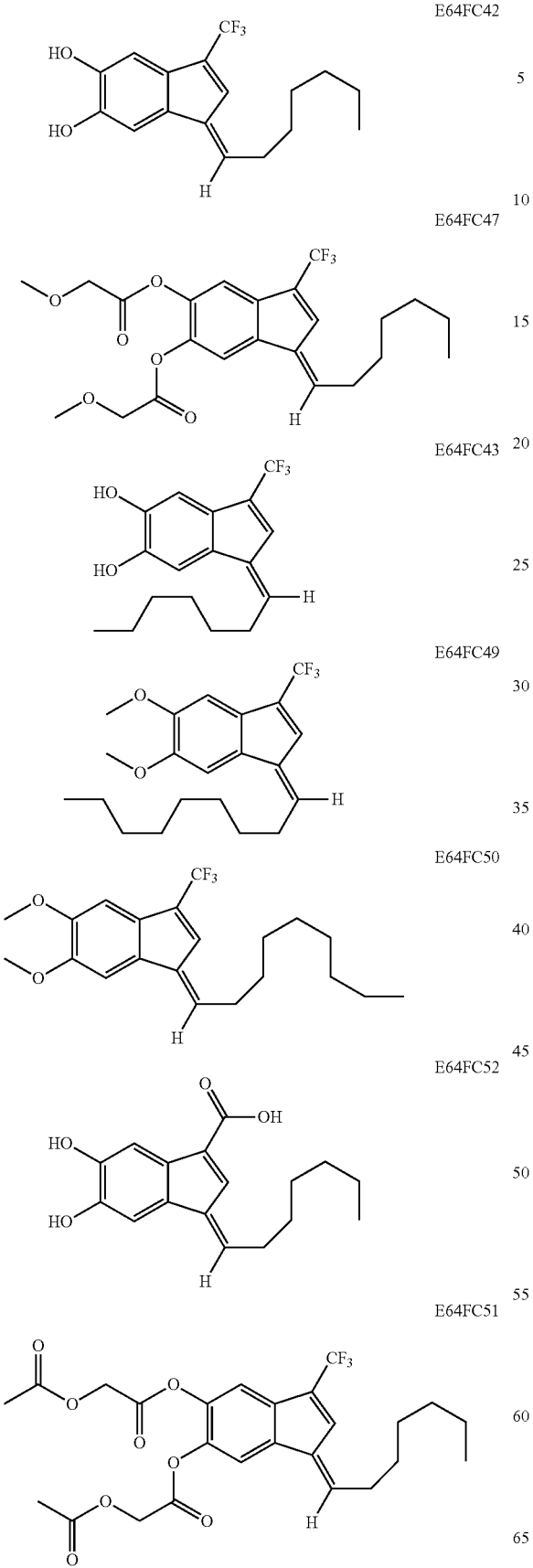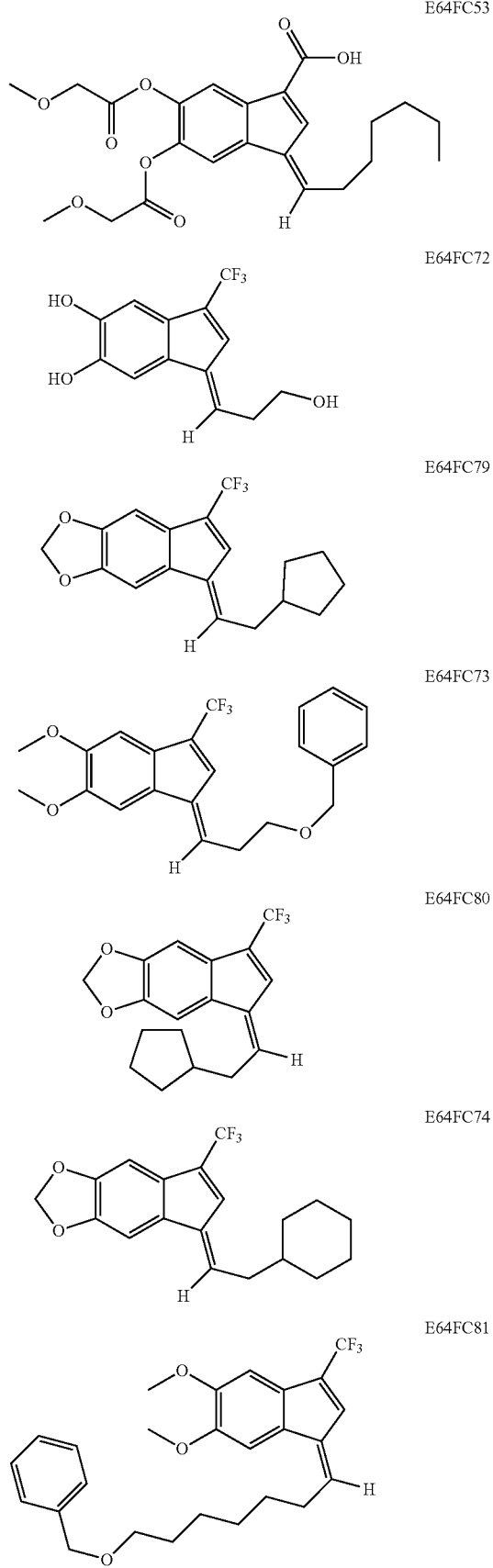

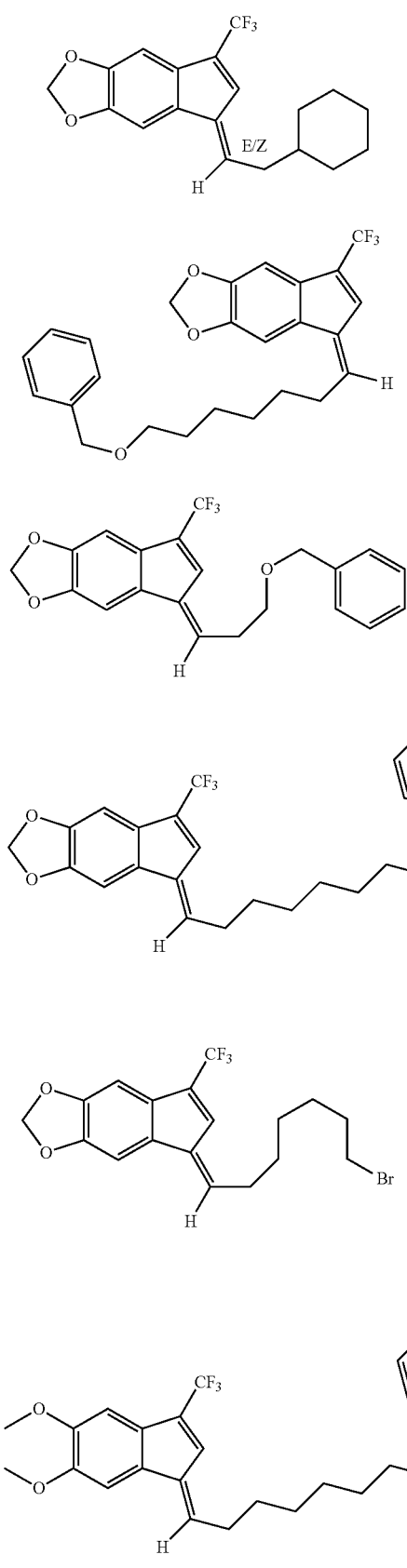
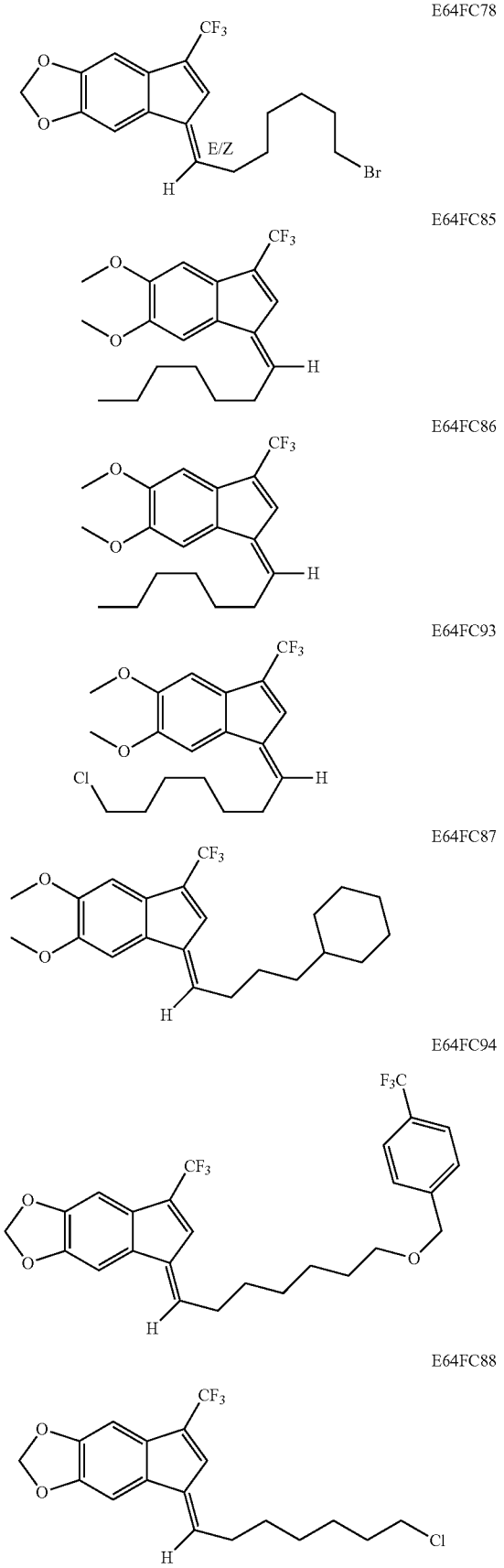

-continued

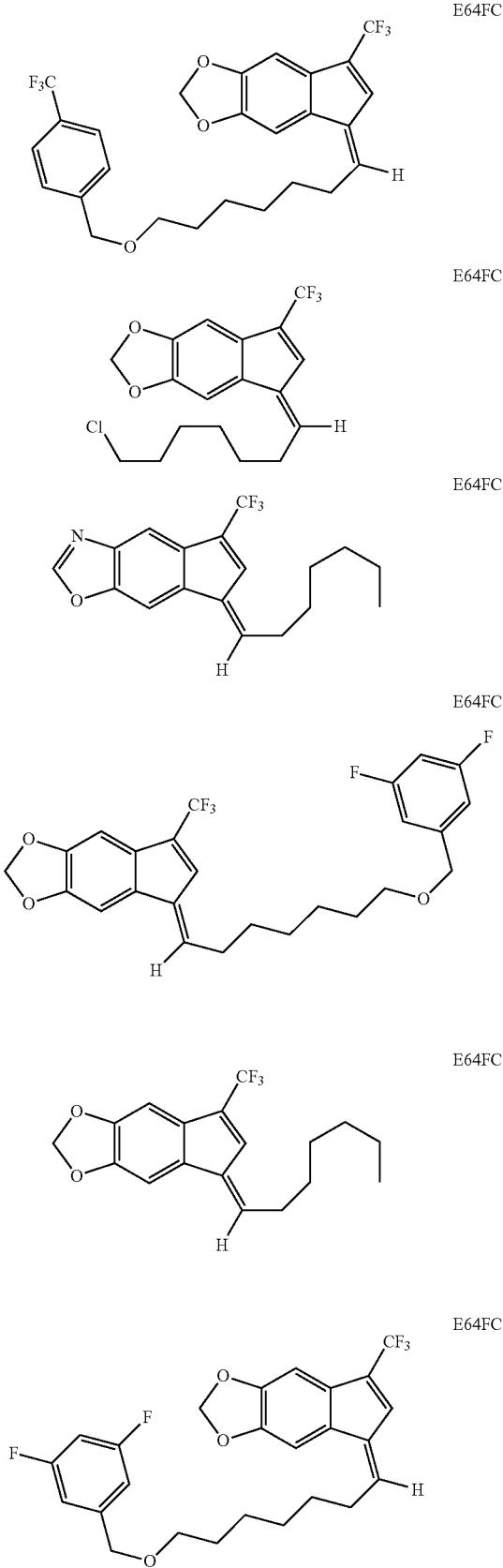

Example 4

Biological Assays

Proteasome Inhibitor Sensitizing Characteristics of Representative Compounds of the Invention Reference is made to FIG. 1. (A) The structures of novel derivatives E64FC26 and E64FC65 are shown. (B) Proteasome inhibitor (PI) resistant MM.1S BzR cells were treated with the E64FC26 at a concentration of 500 nM and a dose range of the PI bortezomib (Btz). Cell viability was measured after 24 hours of treatment. The calculated Btz EC50 for control cells treated with the DMSO vehicle was 45.5 nM compared to and EC50 of 4.7 nM in cells co-treated with E64FC26, a 9.7-fold increase in Btz sensitivity. (C) PANC-1 pancreatic cancer cells were treated with the indicated derivative at a final concentration of 1 μM and a dose range of Btz. Cell viability was measured after a 48 hour treatment time. The Btz EC50 in the presence of DMSO vehicle control was 83.5 nM compared to 9.1 nM in the presence of E64FC26 and 1.8 nM in the presence of E64FC65, corresponding to a 9.2-fold and 46.4-fold increase in Btz sensitivity, respectively. (D) Panels of pancreatic, ovarian, glioma, multiple myeloma, and normal cells were treated with E64FC26 and a dose range of the second generation proteasome inhibitor carfilzomib (Crflz) using a protocol similar to that described above for panels (B) and (C). Crflz EC50 values were extrapolated from dose curves conducted in the presence and absence of E64FC26 and a fold-change was calculated. Each data point represents the fold-change, or the degree of Crflz potentiation, for each cell line tested.

Figure 2:
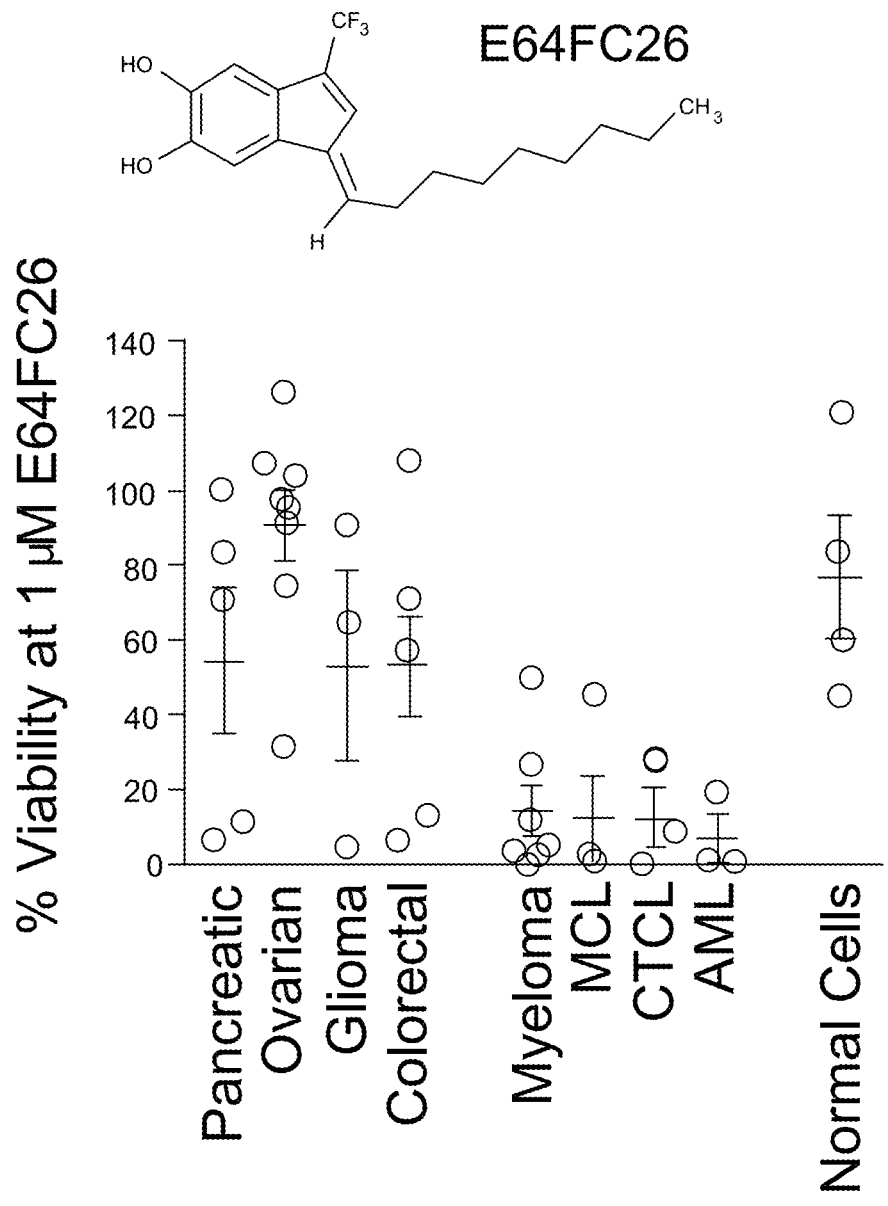
FIG. 2 shows single agent anti-tumor potency of compounds of the invention in a panel of solid and hematological cancer cell lines.

Broad Spectrum Single Anent Anti-Tumor Efficacy of Representative Compounds of the Invention Reference is made to FIG. 2. Cell lines originating from the indicated tumor types were treated with 1 μM E64FC26. After 48 hours of treatment cell viability was measured. Data represent the % viable cells relative to DMSO treated control cell cultures.

Figure 3:
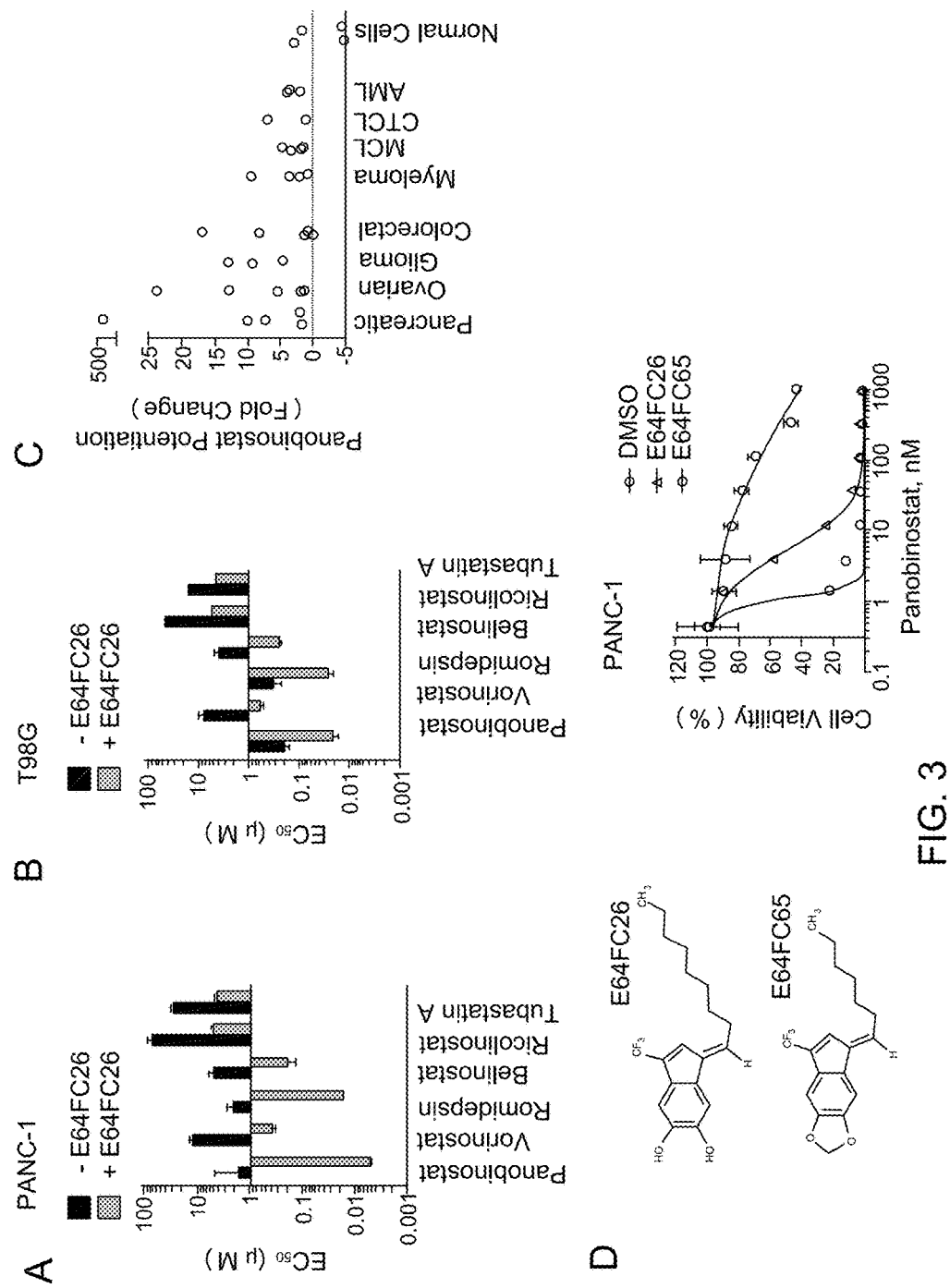
FIG. 3 provides data showing HDACi re-sensitizing characteristics of compounds of the invention in panels of solid and hematological cancer cell types.

HDAC Inhibitor Sensitizing Characteristics of Representative Compounds of the Invention Reference is made to FIG. 3. (A) In PANC-1 pancreatic cancer cells, the cytotoxicity of each of the indicated HDAC inhibitors was evaluated in the presence and absence of 1 μM E64FC26. EC50 values are shown. (B) Similar experiments as described in (A) were conducted using T98G glioblastoma cells. EC50 values for each of the HDAC inhibitor in the presence and absence of 1 μM E64FC26. (C) Panels of the indicated tumor cell types were treated with a dose range of the HDAC inhibitor panobinostat in the presence and absence of 1 μM E64FC26. EC50 values were extrapolated and the relative effect of E64FC26 on panobinostat sensitivity was calculated. Each data point indicated the fold change in panobinostat EC50 for that particular cell line. (D) An example of full panobinostat dose response curves in PANC-1 pancreatic cancer cells are shown. PANC-1 cells were co-treated with DMSO vehicle control, 1 μM E64FC26, or 1 μM E64FC65. The panobinostat EC50 in DMSO treated cells was 453 nM compared to 5.3 nM in the presence of E64FC26 and 1.1 nM in the presence of E64FC65, an increase in panobinostat sensitivity of 85.5-fold and 412-fold, respectively.

In Vive Anti-MM Activity of E64FC26

Figure 4:
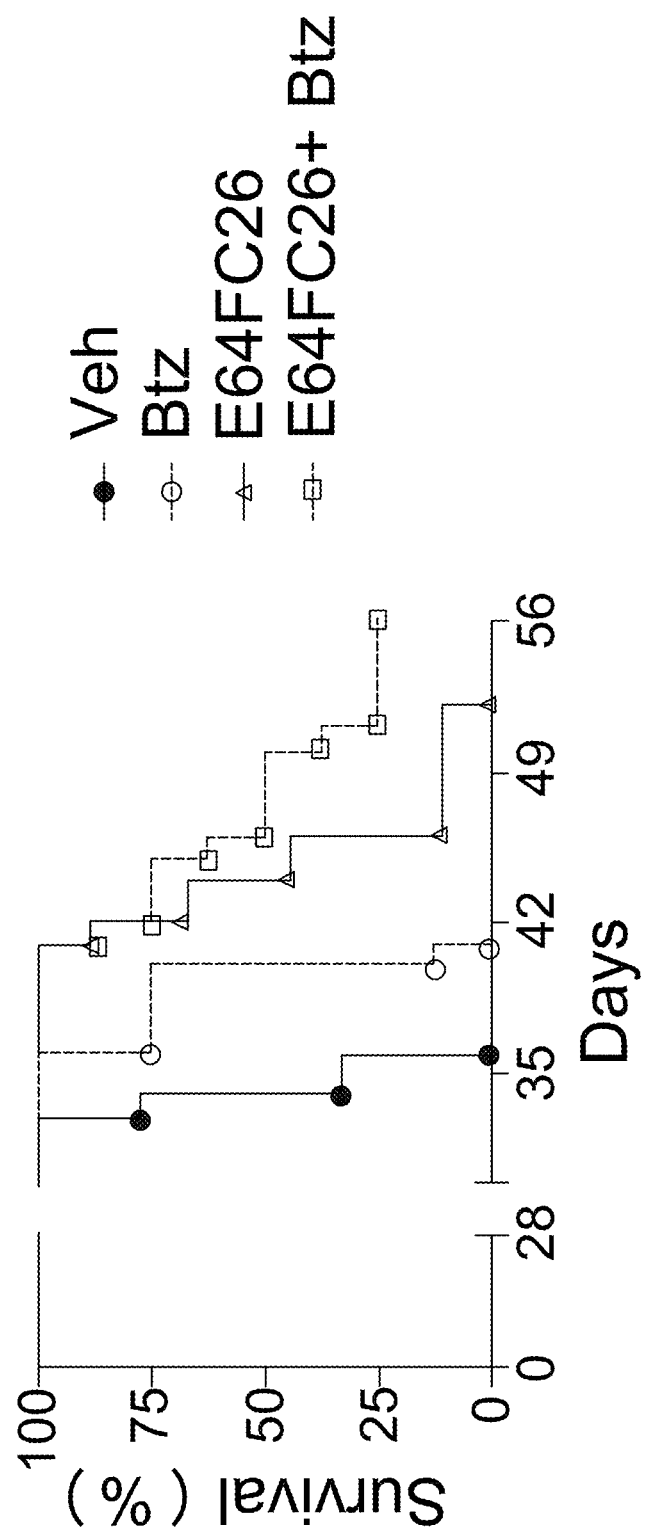
FIG. 4 shows inhibition of PDI activity by E64FC26 and E64FC29 as measured by insulin aggregation.

Reference is made to FIG. 4. The weekly dosing schedules for E64FC26 (2 mg/kg, i.p.) and Btz (0.25 mg/kg, i.p.) are shown. (B) NSG mice were injected i.v. with 1×10$^6$ parental MM.1S cells. After 7 days, mice were randomized into groups (N=8-9) that received treatment with vehicle, E64FC26, Btz, or the combination of E64FC26/Btz using the dosing regimen outlined in Survival data are shown.

Inhibition of PDI Activity by Representative Compounds of the Invention In Vitro Reference is made to the data table in FIG. 5. The table provides the following data for each of the indicated derivatives:

1. EC50 values in cytotoxicity assays in proteasome inhibitor resistant MM cells (MM.1S BzR) as a single agent [column labeled (−) Btz].
2. EC50 values in cytotoxicity assays in proteasome inhibitor resistant MM cells (MM.1S BzR) in combination with 20 nM Btz [column labeled (+) 20 nM Btz].
3. PDI inhibition IC50 in in vitro PDI assays. PDI biochemical assays were performed by incubating 1 μM of recombinant purified PDI for 1 hour at 37 degrees Celsius. 100 μM human insulin and 1 mM DTT were added to initiate the PDI catalyzed aggregation of insulin. The absorbance changes at 650 nm were followed over 45 minutes with measurements taken every minute. The absorbance values in the exponential range were taken and normalized to PDI activity in the absence of inhibitor.

The invention is further described in the following numbered paragraphs:

1. A compound of formula (I):

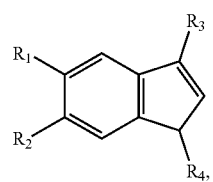

(I)

wherein:
$R_1$ and $R_2$, independently of each other, are hydrogen, hydroxyl, alkyl, alkoxy, methoxy-acetate, phosphate, valine, Gly-Ser, —OC(O)CH$_2$OC(O)CH$_3$, —OC(O)CH$_2$OCH$_3$, —OCH$_2$C(O)C(CH$_3$)$_3$, —OCH$_2$C(O)NH$_2$ or —OCH$_2$C(O)OH; or $R_1$ and $R_2$, together with the carbon atoms to which they are attached, form a 5 to 6-membered ring with one or two ring carbons replaced independently by oxygen or nitrogen;
$R_3$ is hydrogen, hydroxyl, halogen, cyano, —COOH, —C(O)NH$_2$, —C(O)CH$_2$CH$_3$, —C(O)-alkoxy, alkyl, alkoxy, halo-lower alkyl, carboxyl, amide, ester or nitrile; and
$R_4$ is alkyl or alkenyl, said alkyl or alkenyl optionally mono or bi-substituted independently with hydrogen, halogen, hydroxyl, —OCH$_2$-phenyl, cycloalkyl, —OCH$_2$-halophenyl or —OCH$_2$-phenylhaloalkyl,
or a pharmaceutically acceptable salt thereof.

2. The compound according to paragraph 1, wherein $R_1$ and $R_2$, independently of each other, are hydrogen, hydroxyl, alkyl, alkoxy, methoxy-acetate, phosphate, valine, Gly-Ser, —OC(O)CH$_2$OC(O)CH$_3$, —OC(O)CH$_2$OCH$_3$, —OCH$_2$C(O)C(CH$_3$)$_3$, —OCH$_2$C(O)NH$_2$ or —OCH$_2$C(O)OH.

3. The compound according to paragraph 1, wherein $R_1$ and $R_2$, together with the carbon atoms to which they are attached, form a 5 to 6-membered ring with one or two ring carbons replaced independently by oxygen or nitrogen.

4. The compound according to paragraph 1, wherein $R_1$ is hydroxyl.

5. The compound according to paragraph 1, wherein $R_2$ is hydroxyl.

6. The compound according to paragraph 1, wherein both $R_1$ and $R_2$ are hydroxyl.

7. The compound according to paragraph 1, wherein $R_1$ is alkoxy.

8. The compound according to paragraph 1, wherein $R_2$ is alkoxy.

9. The compound according to paragraph 1, wherein both $R_1$ and $R_2$ are alkoxy.

10. The compound according to paragraph 1, wherein $R_3$ is hydrogen, hydroxyl, halogen, cyano, —COOH, —C(O)NH$_2$, —C(O)CH$_2$CH$_3$, —C(O)-alkoxy, alkyl, alkoxy, halo-lower alkyl, carboxyl, amide, ester or nitrile.

11. The compound according to paragraph 1, wherein $R_3$ is amide.

12. The compound according to paragraph 1, wherein $R_3$ is —CF$_3$.

13. The compound according to paragraph 1, wherein $R_4$ is alkenyl.

14. The compound according to paragraph 1, wherein $R_4$ is alkenyl optionally mono or bi-substituted independently with hydrogen, halogen, hydroxyl, —OCH$_2$-phenyl, cycloalkyl, —OCH$_2$-halophenyl or —OCH$_2$-phenylhaloalkyl.

15. A compound, wherein said compound is:

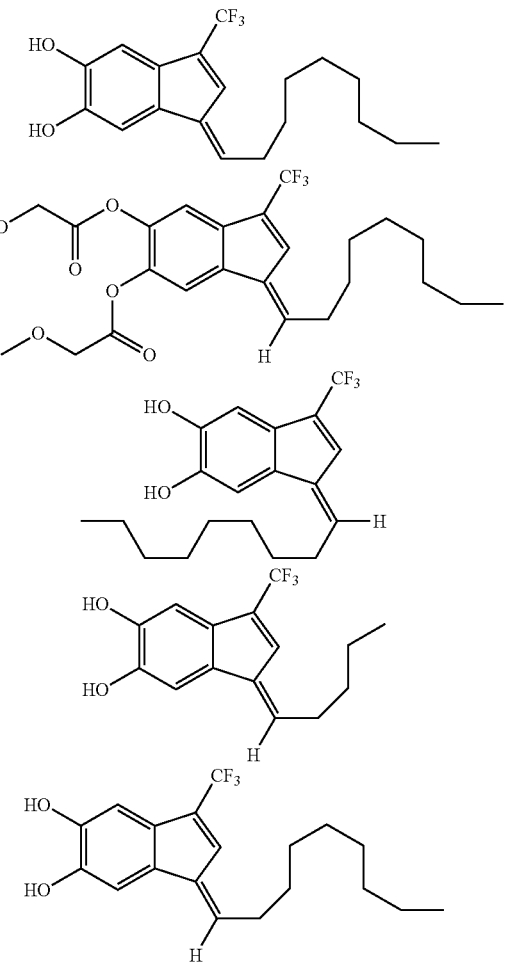

-continued
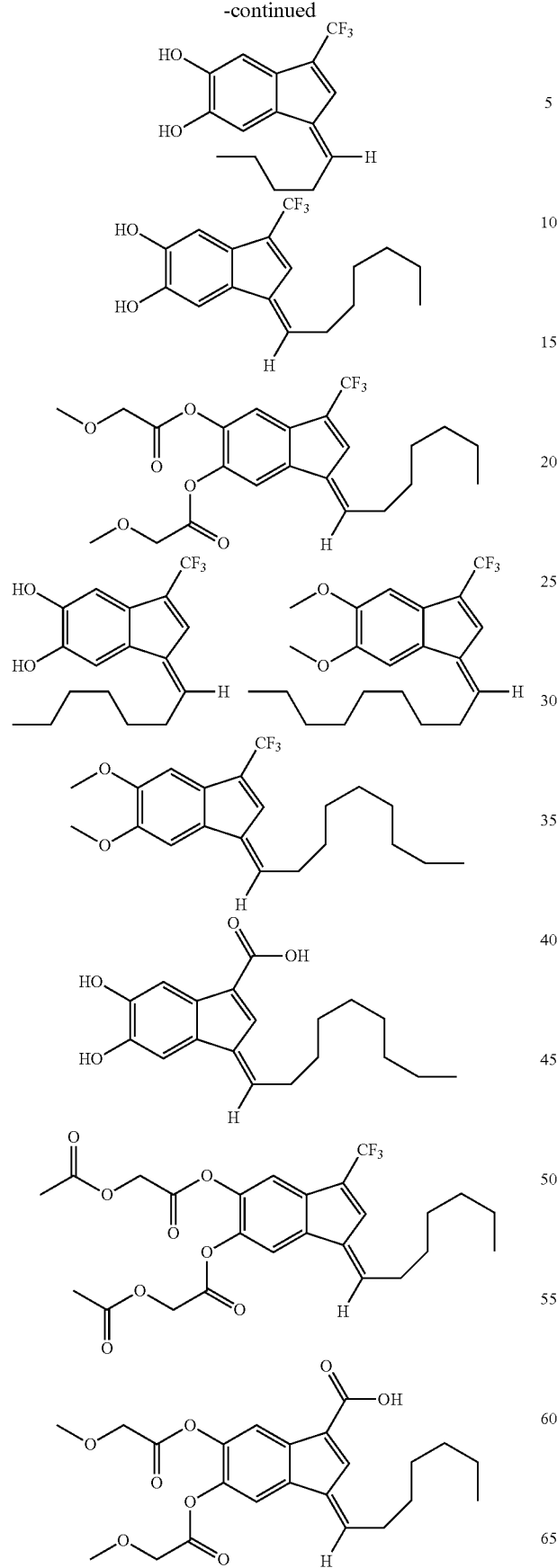
-continued
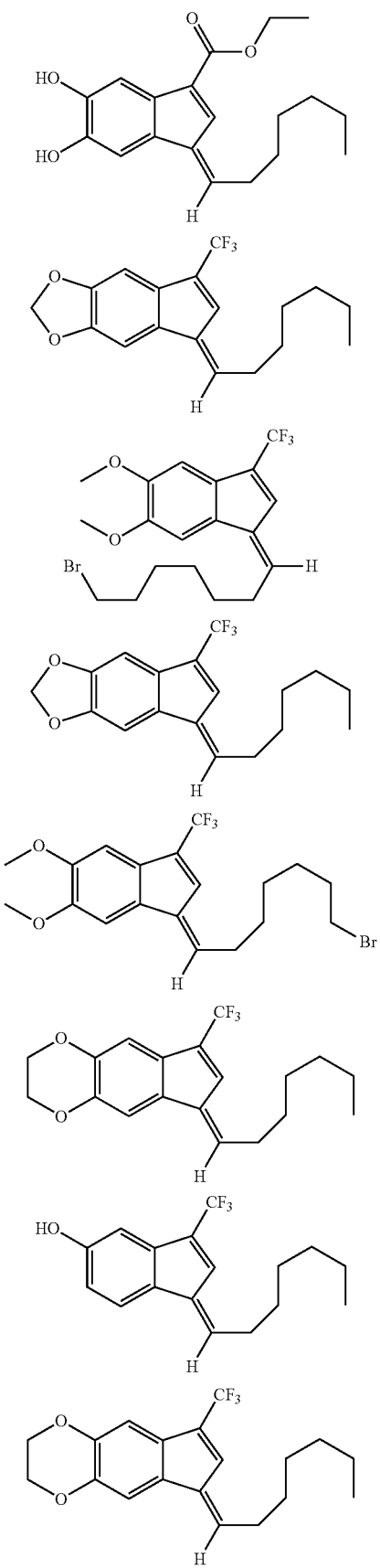

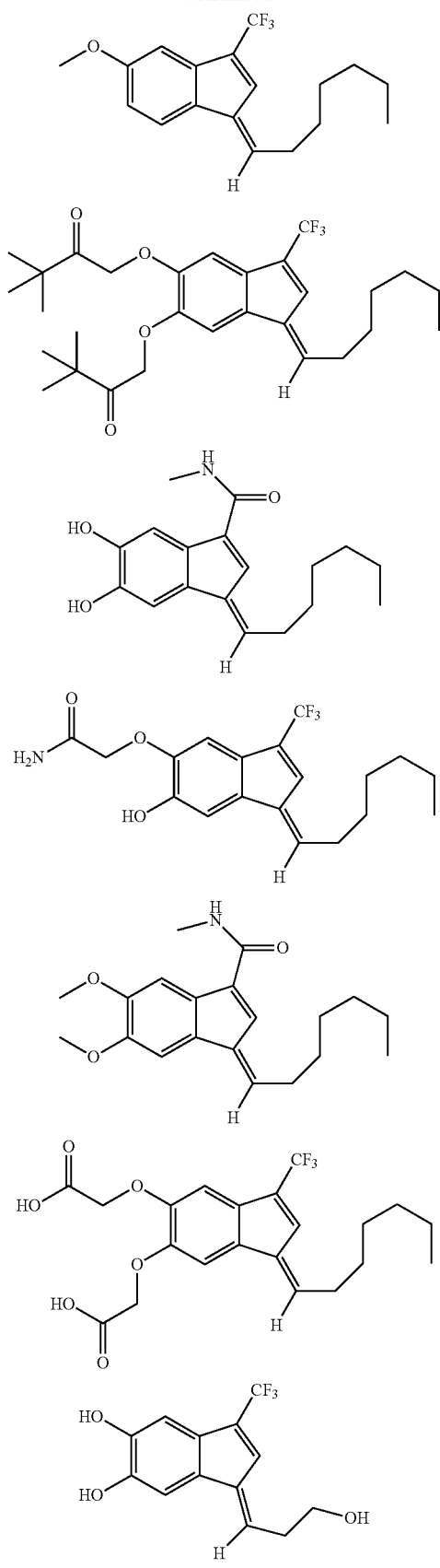
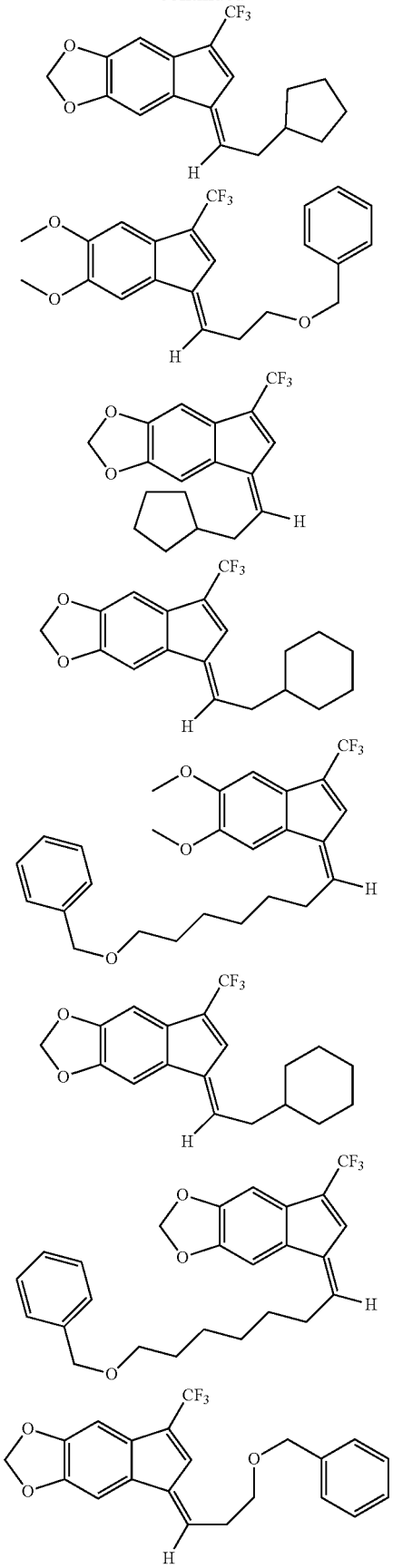

-continued
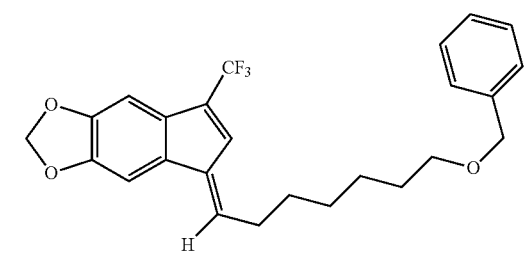
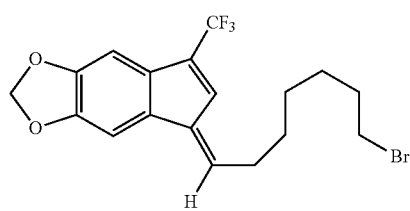
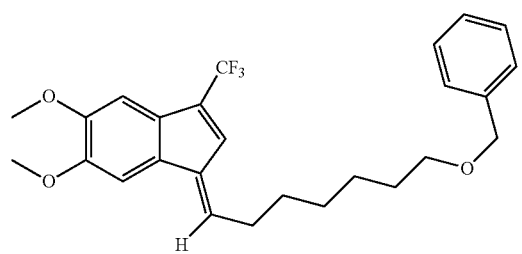
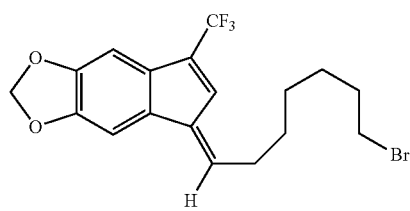
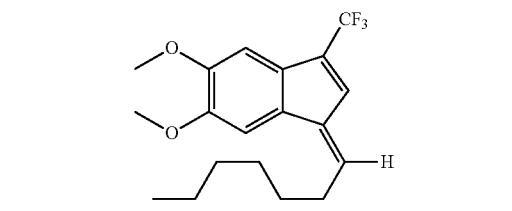
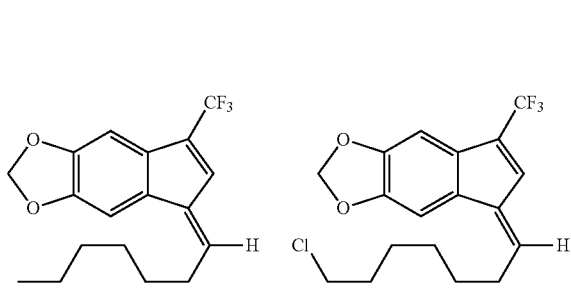
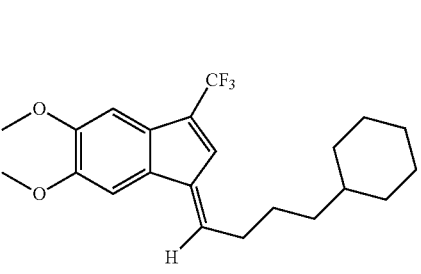
-continued
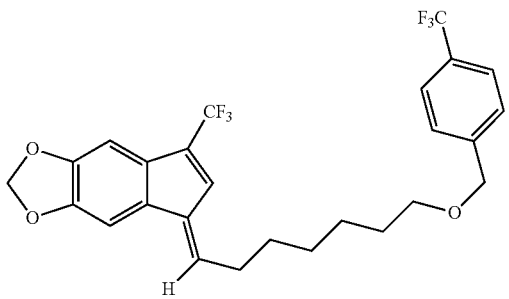
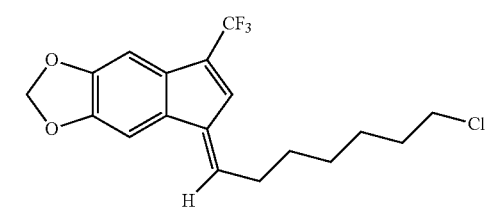
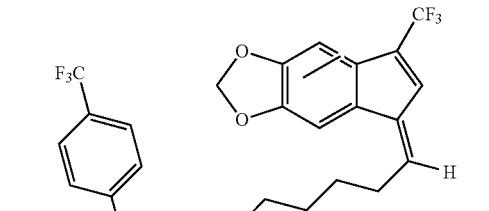
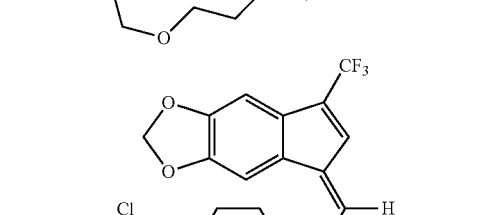
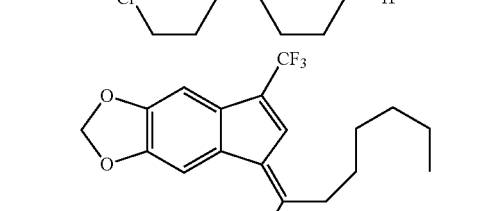
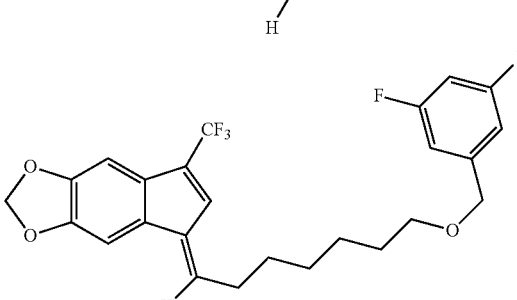
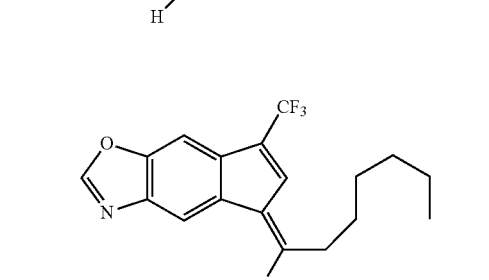

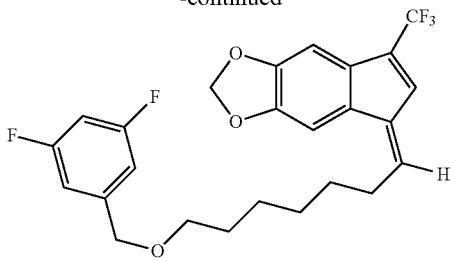

or a pharmaceutically acceptable salt thereof.

16. A pharmaceutical composition, comprising a therapeutically effective amount of a compound according to paragraph 1, or a pharmaceutically acceptable salt thereof, and a pharmaceutically acceptable carrier.

17. A method for the treatment of cancer, comprising the step of administering to a patient in need thereof a therapeutically effective amount of a compound according to paragraph 1, or a pharmaceutically acceptable salt thereof, and a pharmaceutically acceptable carrier.

18. A method for the treatment of multiple myeloma, comprising the step of administering to a patient in need thereof a therapeutically effective amount of a compound according to paragraph 1, or a pharmaceutically acceptable salt thereof, and a pharmaceutically acceptable carrier.

19. A method for enhancing the activity of proteasome and/or HDAC inhibitors, comprising the step of administering to a patient in need thereof a therapeutically effective amount of a compound according to paragraph 1, or a pharmaceutically acceptable salt thereof, and a pharmaceutically acceptable carrier.

20. A method for enhancing the activity of proteasome and/or HDAC inhibitors during treatment of multiple myeloma, comprising the step of administering to a patient in need thereof a therapeutically effective amount of a compound according to paragraph 1, or a pharmaceutically acceptable salt thereof, and a pharmaceutically acceptable carrier.

21. A pharmaceutical composition, comprising a therapeutically effective amount of a compound according to paragraph 15, or a pharmaceutically acceptable salt thereof, and a pharmaceutically acceptable carrier.

22. A method for the treatment of cancer, comprising the step of administering to a patient in need thereof a therapeutically effective amount of a compound according to paragraph 15, or a pharmaceutically acceptable salt thereof, and a pharmaceutically acceptable carrier.

23. A method for the treatment of multiple myeloma, comprising the step of administering to a patient in need thereof a therapeutically effective amount of a compound according to paragraph 15, or a pharmaceutically acceptable salt thereof, and a pharmaceutically acceptable carrier.

24. A method for enhancing the activity of proteasome and/or HDAC inhibitors, comprising the step of administering to a patient in need thereof a therapeutically effective amount of a compound according to paragraph 15, or a pharmaceutically acceptable salt thereof, and a pharmaceutically acceptable carrier.

25. A method for enhancing the activity of proteasome and/or HDAC inhibitors during treatment of multiple myeloma, comprising the step of administering to a patient in need thereof a therapeutically effective amount of a compound according to paragraph 15, or a pharmaceutically acceptable salt thereof, and a pharmaceutically acceptable carrier.

It is to be understood that the invention is not limited to the particular embodiments of the invention described above, as variations of the particular embodiments may be made and still fall within the scope of the appended claims.

The invention claimed is:

1. A compound, wherein said compound is:

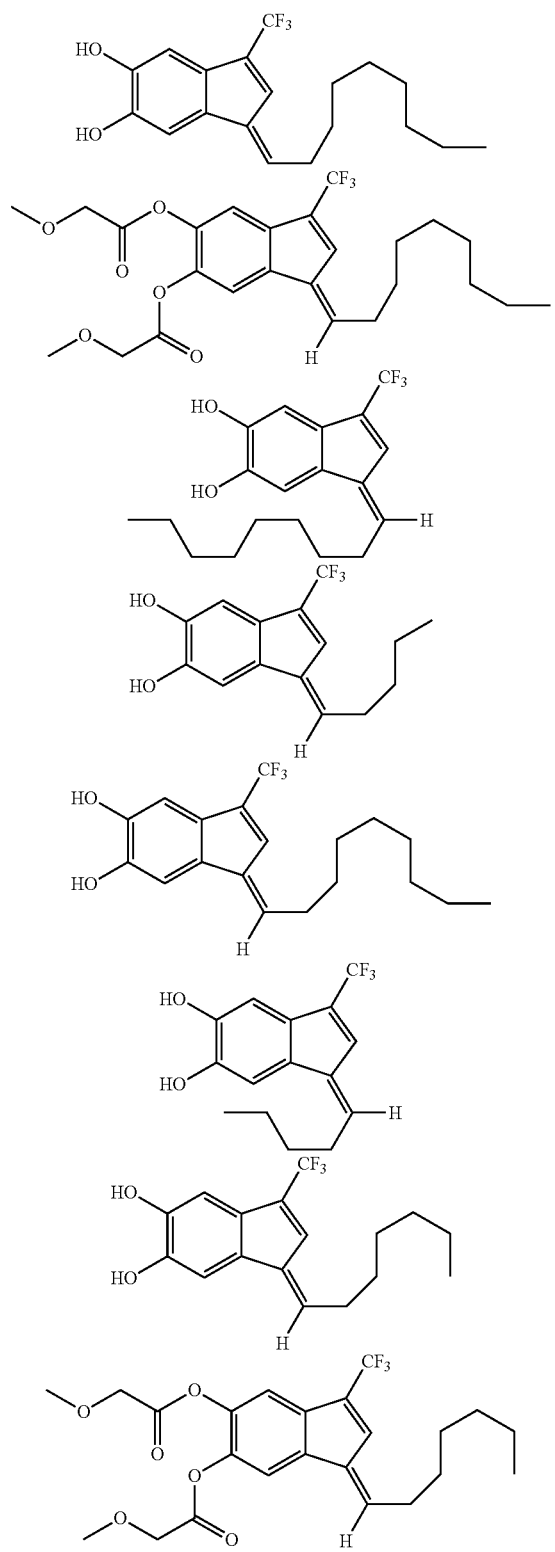

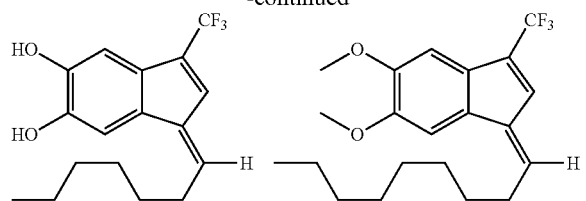
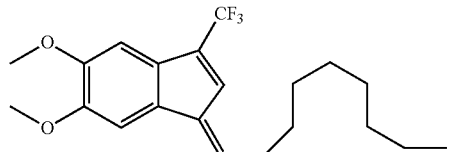
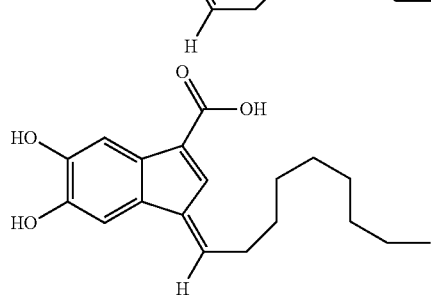
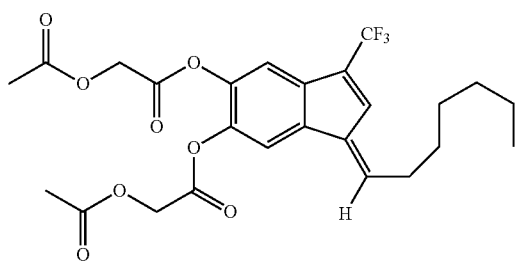
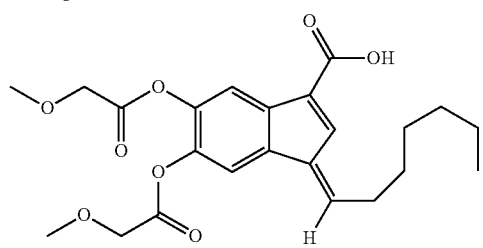
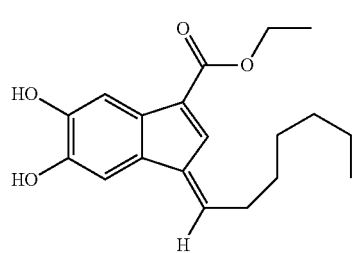
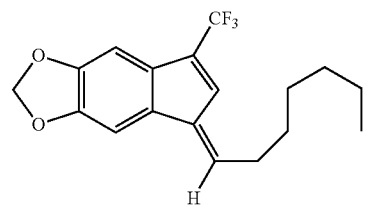
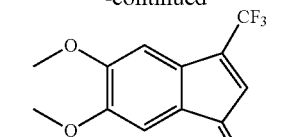
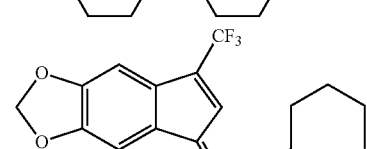
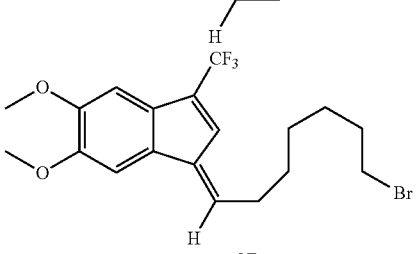
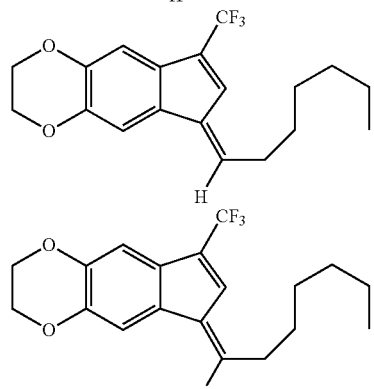
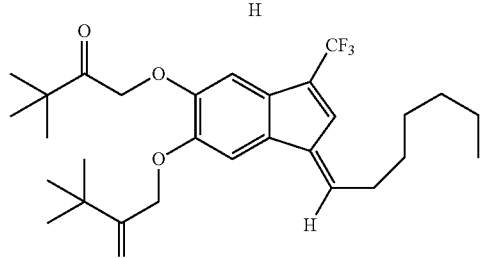
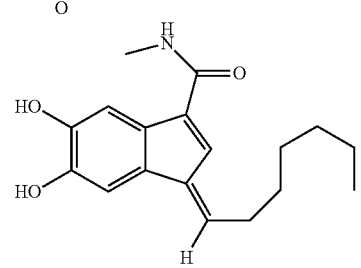
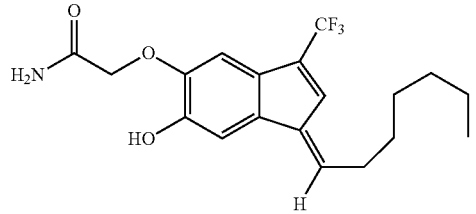

-continued
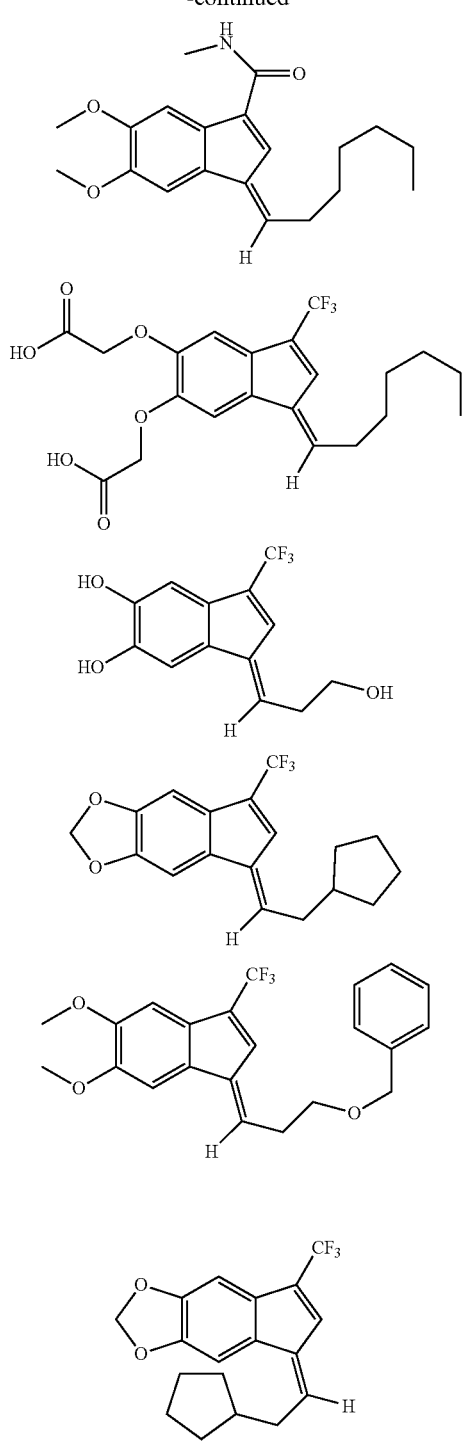
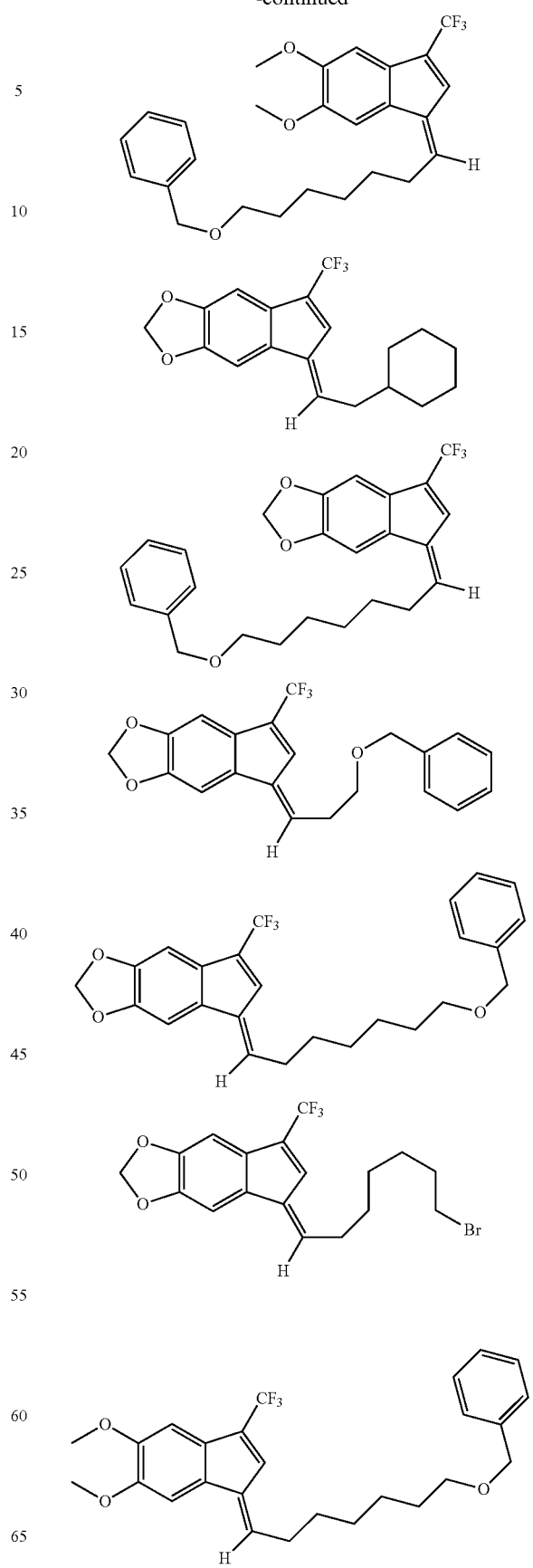

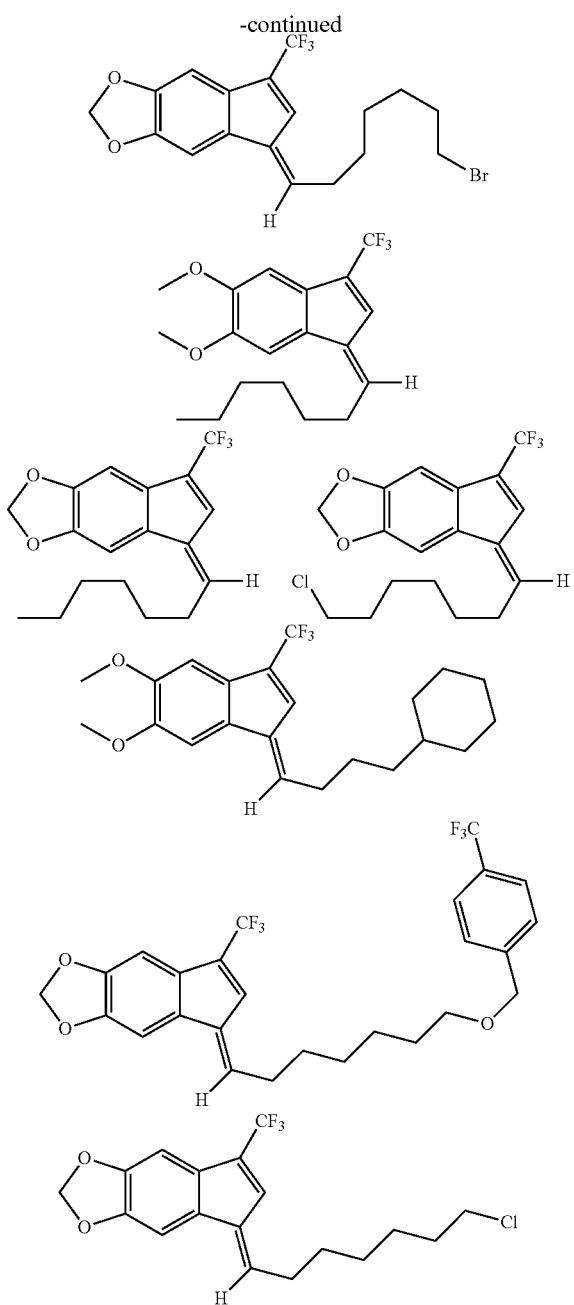
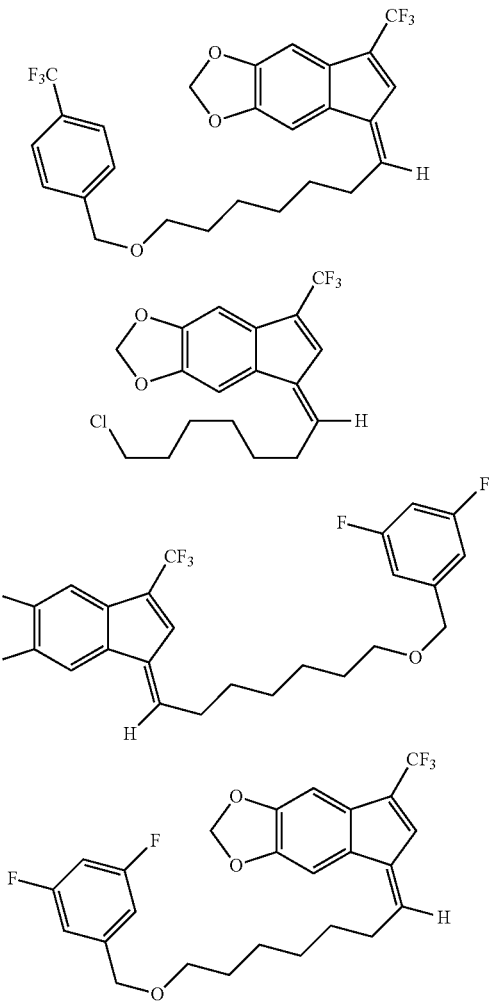
or a pharmaceutically acceptable salt thereof.
2. A pharmaceutical composition, comprising a therapeutically effective amount of a compound according to claim 1, or a pharmaceutically acceptable salt thereof, and a pharmaceutically acceptable carrier.
* * * * *